(12) United States Patent
Bhaskaran et al.

(10) Patent No.: US 10,576,118 B2
(45) Date of Patent: Mar. 3, 2020

(54) FENUGREEK EXTRACT FOR ENHANCING SEXUAL HORMONES IN AGING MALES

(71) Applicant: GE Nutrients, Inc., Irvine, CA (US)

(72) Inventors: Sunil Bhaskaran, Pune (IN);
Ramasamy Varadarajan Venkatesh, Hong Kong (CN); Jith Veeravalli, Irvine, CA (US)

(73) Assignee: GE Nutrients, Inc., Irvine, CA (US)

( * ) Notice: Subject to any disclaimer, the term of this patent is extended or adjusted under 35 U.S.C. 154(b) by 561 days.

(21) Appl. No.: 15/047,464

(22) Filed: Feb. 18, 2016

(65) Prior Publication Data
US 2016/0243179 A1 Aug. 25, 2016

Related U.S. Application Data

(60) Provisional application No. 62/118,314, filed on Feb. 19, 2015.

(51) Int. Cl.
*A61K 36/48* (2006.01)
*A23L 33/105* (2016.01)

(52) U.S. Cl.
CPC ............ *A61K 36/48* (2013.01); *A23L 33/105* (2016.08)

(58) Field of Classification Search
None
See application file for complete search history.

(56) References Cited

U.S. PATENT DOCUMENTS

| 5,997,877 A | 12/1999 | Chang | |
|---|---|---|---|
| 2008/0199517 A1* | 8/2008 | Sunil | A61K 31/7028 424/456 |
| 2012/0295857 A1* | 11/2012 | Goel | A61K 36/48 514/26 |
| 2014/0154346 A1* | 6/2014 | Bhaskaran | A61K 36/48 424/776 |
| 2017/0151271 A1* | 6/2017 | Paxton-Pierson | A61K 31/7048 |

FOREIGN PATENT DOCUMENTS

| IN | 2013 DE03119 | * 12/2015 |
| KR | 1579845 B1 | * 12/2015 |
| WO | 2014/089344 A2 | 6/2014 |

OTHER PUBLICATIONS

Steels, E. et al. Physiological Aspects of Male Libido Enhanced by Standardized Triogonella foenum-graecum Extract . . . Phytotherapy Research 25(9)1294-1300, Sep. 2011. (Year: 2011).*
Aswar U. et al. Effect of Furostanol Glycosides from Trogonella foenum-graecum om the Reproductive System of Male Albino Rats. Phytotherapy Research 24(1)1482-1488, Oct. l, 2010. (Year: 2010).*
Nguyen S. et al. Pulmonary Embolism Secondary to Testerosterone Enhancing Herbal Supplement Use. Cureus 9(8), Aug. 2017. (Year: 2017).*
J. Kellogg Parsons, Benign Prostatic Hyperplasia and Male Lower Urinary Tract Symptoms: Epidemiology and Risk Factors, 5 Curr. Bladder Dysfunct. Rep. 212 (2010).
A. Morales et al., Adding to the controversy: Pitfalls in the diagnosis of testosterone deficiency syndromes with questionnaires and biochemistry, 10 The Aging Male 57 (2007).
Alvin M. Matsumoto, Andropause: Clinical Implications of the Decline in Serum Testosterone Levels With Aging in Men, 57A J. Gerontology M76 (2002).
Alvaro Morales et al., Andropause: A Misnomer for a True Clinical Entity, 163 J. Urology 705 (2000).
L. A. J. Heinemann et al., A new 'aging males symptoms' rating scale, 2 The Aging Male 105 (1999).
Isolde Daig et al., The Aging Males' Symptoms (AMS) scale: review of its methodological characteristics, 1 Health & Quality of Life Outcomes (2003).
Male Sexual Dysfunction: Pathophysiology & Treatment (Fouad R. Kandeel ed., Informa Healthcare 2007).
Letitia Anne Peplau, Human Sexuality: How Do Men and Women Differ?, 12 Curr. Directions in Psychological Sci. 37 (2003).
Sonia Puri & Amarjeet Singh, Adam and AMS Scale for Assessing Andropause Among Aging Indian Men, 7 Int'l J. Pharmacy & Pharm. Scis. 453 (2014).
R. Sodergard et al., Calculation of free and bound fractions of testosterone and estradiol-17 beta to human plasma proteins at body temperature, 16 J. Steroid Biochem. 801 (1982).
Amanda Rao et al., Testofen, a specialised Trigonella foenum-graecum seed extract reduces age-related symptoms of androgen decrease, increases testosterone levels and improves sexual function in healthy aging males in a double-blind randomised clinical study, The Aging Male (2016).
Steels, E., et al., "Phsiological Aspects of Male Libido Enhanced by Standaradized Trigonella foenum-graecum Extract and Mineral Formulation," Phytother. Res. (2011) 1294-1300.
Murray, M., Is Andropause Real? Better Nutrition. Feb. 2014; pp. 30-31.
Vaibhav, G., et al., Antidepressant-like effect of 4-hydroxyisoleucine from Trigonella foenum gracecum L. seeds in mice; Biomedicine & Aging Pathology 2 (2012) 121-125.
Saini, D., et al., Evaluation of Nootropic Activity of Trigonella foenum Leaves in Mice; International Journal of Pharmacy and Pharmaceutical Sciences, vol. 4, Issue 4, 2012.
Subhashini, N.,et al., Antioxidant Activity of Trigonella Foenum Graecum Using Various In Vitro and Ex Vivo Models; International Journal of Pharmacy and Pharmaceutical Sciences, vol. 3, Issue 2, 2011.
Table of Laboratory Reference Ranges, Endocrine Society, Washington, D.C. (2005).

(Continued)

*Primary Examiner* — Ralph J Gitomer
(74) *Attorney, Agent, or Firm* — Amin Talati Wasserman LLP; George M. Carrera, Jr.

(57) ABSTRACT

Methods of improving or enhancing sexual conditions in an aging male human subject, by administering fenugreek or fenugreek seeds, or an extract of fenugreek or fenugreek seeds, are described. Methods of improving sexual functions, preventing further decline of sexual hormones, and/or improving sexual hormonal level in an aging male human subject, by administering fenugreek or fenugreek seeds, or an extract of fenugreek or fenugreek seeds, are also described.

3 Claims, 3 Drawing Sheets

(56) References Cited

OTHER PUBLICATIONS

Santos-Casado, M.D., et al. "Systematic review of gender bias in the clinical trials of new long-acting antipsychotic drugs," J. Clin. Psychopharmacology (May/Jun. 2019) vol. 39 (3), 264-272. (Abstract Only).

Liu, et al., "Women's involvement in clinical trials: historical perspective and future implications," Pharmacy Practice Jan.-Mar. 2016; 14(1): 708.

* cited by examiner

FENUGREEK EXTRACT FOR ENHANCING SEXUAL HORMONES IN AGING MALES

This application claims the benefit of U.S. Provisional Application No. 62/118,314, filed on Feb. 19, 2015. The disclosure of this prior application is incorporated herein by reference in its entirety for all purposes.

TECHNICAL FIELD

The present invention relates to methods of enhancing psychological, somatic, and sexual conditions in an aging male human subject by administering a fenugreek extract. The present disclosure relates to reduction in symptom severity, improvement in sexual functions, prevention of further decline of sexual hormones and improvement in sexual hormonal level in an aging male human subject by administration of a fenugreek extract.

BACKGROUND

Aging encompasses problems, especially psychological, behavioral, systemic, and sexual dysfunction. The process of aging not only involves disabilities and health related morbidities but also a wide array of psychological aspects. The process in men involves modifications in testosterone levels, with psycho-physical outcomes of variable intensity.

The main action of the steroid hormone testosterone is the intensifying of the primary and secondary sex characteristicts of human males, as well as the maintaining of the functions associated therewith. Apart from this main effect testosterone has a number of secondary effects, which are of great importance for the stressability and performance characteristics of the human organism. These include the maintaining of an anabolic metabolic situation, the restoration of the performance of human males following exhausting exercise, and increasing the psychophysiological stressability and stress resistance.

The action mechanisms of testosterone have been investigated in detail. The secondary effects on the psychophysiological state have, according to research, been attributed to the presence of testosterone receptors in the central nervous system.

Over 90% of the testosterone in the blood is bound to protein, and the biologically active component is free testosterone, representing 4% to 8% of the total concentration in the blood. The testosterone concentration in the blood is subject to a physiologically daily cycle (maximum concentration in the morning), a seasonal cycle (lowest concentration in May), and influences by living circumstances and aging processes.

The overall testosterone concentration in the blood is individually very stable under normal conditions. Intense physical effort, long-lasting stressful situations, and unfavorable diet lower the blood level of testosterone. With increasing age, and in particular, from about the age of thirty in human males, there is a reduction of the free testosterone concentration. It has been established that testosterone decreases by approximately 1% per year after age thirty (30).

In human males, small amounts of estrogen are produced by aromatization of testosterone both in the testes and peripheral tissues. Although present in only small amounts, generally less than one-fourth to one-tenth of that in pre-menopausal women, estrogen may play a role in the regulation of the male hypothalamic pituitary gonad axis, bone development, development of the prostate, and metabolic function. In the hypothalamus, conversion of testosterone to estrogen results in negative feedback on gonadotropin release. Estrogens thus normally reduce circulating testosterone and anti-estrogens result in corresponding increases. As men age, the proportion of fat to lean tissue gradually increases. Aromatization of testosterone in fat may lead to gradually increased estrogen-to-testosterone ratios and negative feedback that reduces total testosterone levels.

These changes lead to a reduced general performance, to higher time requirements for restoring the organism after exhaustive exercise, and to a reduction of the psychophysiological stressability and stress resistance. Research on physically and cyclically highly stressed persons has revealed that a rise in the testosterone level in the upper part of the individual physiological fluctuation range leads to a cancelling out of this negative situation, and to an increase in the general performance characteristics. The increase in the testosterone level in human males has consequently become part of preventative and therapeutic concepts in medical treatment of aging males.

There are several pharmaceutical methods to restore testosterone levels in humans with suboptimal levels. Many of these have disadvantages however. Testosterone esters in oil depot form have been used as injections for decades, however these injections can be inconvenient and often painful. These depot injections also result in inconsistent blood levels as a supraphysiological surge is seen soon after injection, but by the time the next injection is due, the levels often have dropped down below standard physiological levels. This is in contrast with testosterone levels under normal conditions, which are quite stable within mild release pulses of approximately 90 minute duration. Supraphysiological surges that are seen with injectable preparations may increase the incidence of undesirable side effects (i.e. prostate hypertrophy) as well as cause an amplified shutdown of the hypothalamic/pituitary testicular axis ("HPTA").

Other pharmaceutical methods of androgen replacement therapy include synthetic oral androgen derivatives. These compounds (i.e. methyltestosterone and fluoxymesterone) are altered in the 17 alpha position of the steroid molecule with an alkyl group. This alkyl group renders the steroid impervious to oxidation of the 17 beta hydroxyl group in the liver and therefore greatly improves its oral bioavailability compared to the non-alkylated steroids. However, this structural modification also has been associated with a greatly increased risk of hepatotoxicity. Therefore, these synthetic compounds are far from an ideal solution.

Hypogonadism is recognized as a common occurrence in older males. A number of studies have suggested that hypogonadism may result in some of the observed decrements in muscle and skeletal mass associated with advancing age. The prevalence of hypogonadism in men is approximately 20% in men in their seventh decade with biochemical evidence of androgen deficiency, which increases to 50% of men in the eighth decade of life.

According to Indian Census 2011, India has the largest number of people with ages above sixty (60) years and these account for 9% of India's total population. By the year 2050, the number of elderly people in India will grow to 25% of the population, i.e., from 62 million to 240 million (Government of India: "Population Totals" Census; 2011. Accessed: 10 Sep. 2013).

By the year 2030, 20% of the U.S. population will be sixty-five (65) years of age or older, a figure that will include more than 20 million men. Significantly, the fastest growing segment of the older adult population is the oldest age group:

those older than 85 years of age. Current estimates indicate that the number of individuals eighty (80) years of age or older in the United States will rise from 9.3 million in 2000 to 19.5 million in 2030, an increase of more than 100% (J. Kellogg Parsons, *Curr. Bladder Dysfunct. Rep.* (2010) 5:212-218).

Andropause or "male climacteric" is defined herein as a clinical and biochemical syndrome associated with aging and characterized by a set of typical symptoms, as well as testosterone deficiency.

The symptoms include alterations in the sexual, physical, and mental domains. The sexually related manifestations include reduced libido, erectile dysfunction, and decreased ejaculatory force and volume. The condition also results in easy fatigability, lethargy, hot flushes, blushing and sweating, depression, mood swings, nervousness, anxiety and irritability, poor concentration/memory, adiposity, reduction in strength, and bone/joint complaints. Testosterone deficiency has been associated with hip fracture and bone mass has been correlated with testosterone levels in older persons.

Although measurement of free testosterone is the gold standard for diagnosis of primary and secondary hypogonadism, due to financial and technical constraints it may not be possible to measure free testosterone levels in all of the situations. Therefore, attempts were made to develop certain noninvasive or non-interventional tools to diagnose hypogonadism on the basis of clinical presentation. These tools were developed to screen men who exhibited these general symptoms for a suite of other possible deficiencies, so that the chance of making the correct clinical diagnosis could be improved.

Morales et al. have described andropoause as a misnomer, and suggested a new term, Androgen Deficiency of the Aging Male ("ADAM"), a questionnaire that has a sensitivity of 88% and a specificity of 60% in men (Morales et al., 10(2) AGING MALE 57-65 (2007)), while some others preferred the term Partial Androgen Decline in Aging Males ("PADAM") or Aging-Associated Androgen Deficiency ("AAAD") (Matsumoto, *Andropause: Clinical implications of the decline in serum testosterone levels with aging men,* 57A J. GERONTOLOGY: MED. SCIS. M76-99 (2002); Morales et al., *Andropause: A misnomer for a true clinical entity,* 163 J. UROLOGY 705-12 (2000)). The most widely used tools including Aging Males' Symptoms ("AMS") scale and the Derogatis Interview for Sexual Functioning ("DISF").

The AMS scale is a health-related quality of life scale ("HRQoL") and was originally developed in Germany in 1999 (Heinemann et al., A New '*Aging Male's Symptoms*' (*AMS*) *Rating Scale,* 2 AGING MALE 105-14 (1999)). The scale was designed as a self-administered scale: (a) to assess symptoms of aging (independent of those that are disease-related) between groups of males under different conditions; (b) to evaluate the severity of symptoms over time; and (c) to measure changes pre- and post-androgen therapy. The AMS scale was developed in response to the lack of fully standardized scales to measure the severity of aging symptoms and their impact on HRQoL in males, specifically. See Daig et al., *The Aging Males' Symptoms (AMS) scale: review of its methodological characteristics,* 1 HEALTH & QUALITY OF LIFE OUTCOMES 77 (2003), and references cited therein.

The DISF is a coordinated set of brief-matched instruments designed to provide an estimate of the quality of an individual's current sexual functioning. It comprises twenty-five (25) questionnaire items and reflects quality of sexual functioning in the multi-domain format. All of the instruments in the DISF series are designed to be interpreted at three distinct levels: discrete items, functional domains, and aggregate summary (total) score. The DISF items are arranged into five primary domains of sexual functioning: sexual cognition/fantasy, sexual arousal, sexual behavior/experience, orgasm, and sexual drive/relationship. In addition, an aggregate DISF total score is computed that summarizes quality of sexual functioning across the five primary DISF domains. See MALE SEXUAL DYSFUNCTION: PATHOPHYSIOLOGY & TREATMENT 255 (Fouad R. Kandeel ed., Informa Healthcare 2007).

First, on a wide variety of measures, men show greater sexual desire than do women. Second, compared with men, women place greater emphasis on committed relationships as a context for sexuality. Third, aggression is more strongly linked to sexuality for men than for women. Fourth, women's sexuality tends to be more malleable and capable of change over time. Letitia Anne Peplau, 12 AM. PSYCHOLOGICAL SOC'Y: CURR. DIRECTIONS IN PSYCHOLOGICAL SCI. 37-40 (2003).

Stated broadly, women are more strongly affected by estrogen and progesterone, males by testosterone. These hormones are contrasting in their effects. Progesterone, for instance, is a female growth hormone and also the bonding hormone. Testosterone is the male growth hormone and also the sex-drive and aggression hormone. Hence it is not likely that the drugs effective for female libido would show efficacy for male libido as well.

Fenugreek (*Trigonella foenum-graecum*) has attracted considerable interest as a natural source of soluble dietary fiber and diosgenin (sapogenins). The fenugreek seed constains a central hard, yellow embryo surrounded by a corneous and comparatively large layer of white, semi-transparent endosperm. This endosperm contains galactomannan gum. The endosperm is surrounded by a tenacious, dark brown husk. The color of the gum fraction depends on the amount of outer husk (brown color) and cotyledon (yellow color) present.

There are commercial uses for the various fractions of the fenugreek seed. The commercial fenugreek oleoresins are used as an ingredient for imitation maple flavors and are effective in butter, butterscotch, black walnut, nut, and spice flavors. Another fraction of the fenugreek seed has been found to be a quantity of saponins. Fenugreek seed saponins, including sapogenins, are steroidal in nature, with diosgenin as the main sapogenin Disogenin is used by the drug industry as a precursor to progesterone (steroid hormones), which is used in the manufacturing of oral contraceptives.

U.S. Pat. No. 5,997,877 to Chang, and references cited therein, discloses a process for the recovery of substantially pure extracts from fenugreek seed, said process comprising mixing the fenugreek seed with a solvent for a period of contact time at a certain temperature such that certain seed components of the fenugreek seed are absorbed by the solvent; separating extracted fenugreek seed from the solvent, which solvent now contains extracted seed components; and separating the extracted seed components from the solvent, to yield seed components and spent solvent.

WO 2014/089344A2 to Bhaskaran et al., and references cited therein, discloses a method of enhancing female sexual drive and libido by administering a fenugreek extract but it does not provide any motivation to use the fenugreek extract in male libido.

Therefore, if a use of fenugreek, fenugreek seeds, or extracts thereof, to enhance psychological, somatic, and sexual conditions in an aging male human subject could be found, this would represent a useful contribution to the art. Further, if a use of fenugreek, or extracts thereof, to reduce symptom severity, improve sexual functioning, prevent further decline of sexual hormones, and/or improve sexual hormonal level in an aging male human subject could be found, this would represent a useful contribution to the art.

DETAILED DESCRIPTION

Figure 1:
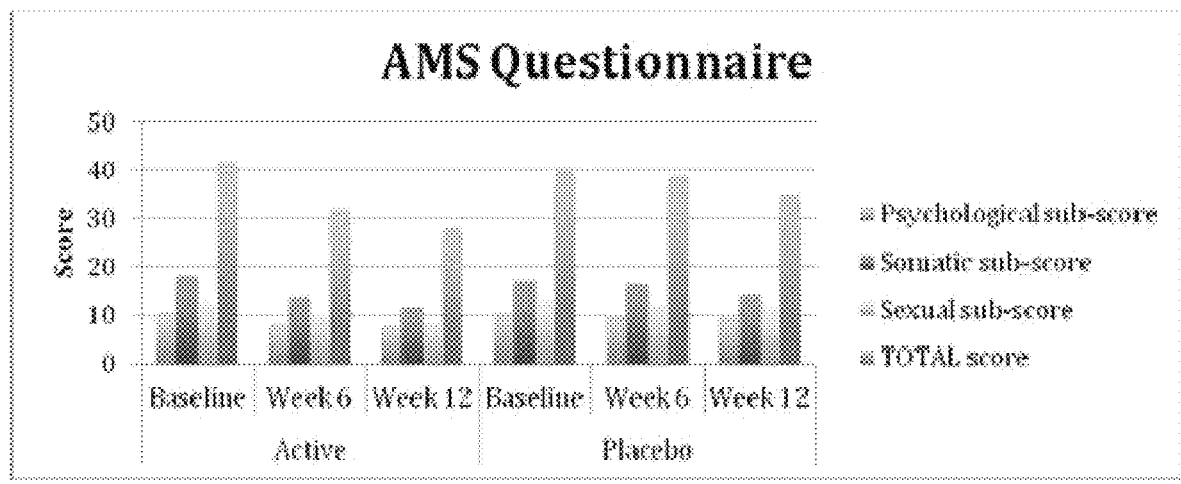
FIG. 1 depicts a bar chart showing AMS scores for male subjects treated orally BID with 300 mg Fenugreek seed extract vs. placebo. Subscores are listed top to bottom in the legend, corresponding to left to right in the bar graph.

In one aspect, the invention relates to methods of enhancing psychological, somatic, and sexual conditions in aging males by administering a fenugreek extract.

In one embodiment, the invention relates to methods of reducing psychological or somatic conditions and enhancing sexual conditions in aging males by administering a fenugreek extract.

The present disclosure also relates to enhancement of psychological, somatic, and sexual conditions in aging males, wherein psychological conditions include depression, mood swings, nervousness, anxiety, irritability, and poor concentration/memory.

The present disclosure also relates to enhancement of psychological, somatic, and sexual conditions in aging males, wherein somatic conditions include fatigability, hot flushes, blushing and sweating, adiposity, reduction in strength, and bone/joint complaints.

The present disclosure also relates to enhancement of psychological, somatic, and sexual conditions in aging males, wherein sexual conditions include reduced libido, erectile dysfunction, and decreased ejaculatory force and volume.

The present disclosure further relates to reduction in symptom severity, improvement in sexual functions, prevention of further decline of sexual hormones, and improvement or enhancement in sexual hormonal level in aging males by administration of a fenugreek extract.

The present disclosure also relates to improvement in sexual functions, wherein sexual functions include sexual cognition, sexual arousal, sexual experience, orgasm, and sexual relationship.

The present disclosure also relates to prevention of further decline of sexual hormones including, but not limited to, Testosterone and Free Testosterone.

The present disclosure also relates to enhancement in sexual hormonal level such as, but not limited to, Testosterone, Free Testosterone, Estrogen, and Prolactin.

The methods described herein may be further understood in connection with the following Examples.

EXAMPLE 1

A double-blind, randomized, placebo-controlled study of the efficacy of an orally-dosed herbal formulation, including Fenugreek, on symptoms of Andropause and serum testosterone levels in otherwise healthy aging males was conducted.

Study Design 120 healthy male subjects, aged 40-75, were recruited through the CRO's subject database and public media. Comprehensive screening was performed after an initial medical assessment including lifestyle questions, current medications, medical history, and a basic physical examination. Subjects were screened against the following criteria.

Inclusion criteria:

Male aged between 45-75;

Otherwise healthy;

Written informed consent from the subject.

Exclusion criteria. Subjects will be excluded for any one of the following reasons: known hypersensitivity to herbal drugs/nutritional supplements/foods; erectile dysfunction or any physical disability that may limit sexual function; received any treatment/therapy (including testosterone) for any sexual disorder during last six (6) months; received/prescribed coumadin (Warfarin), heparin, dalteparin, enoxaparin, or other anticoagulation therapy; received/prescribed levodopa (Sinemet) for Parkinson's Disease or calcipotriene (Dovonex) for Psoriasis; diagnosed with hypertension and received/prescribed antihypersentive medications; diagnosed severe renal and/or hepatic insufficiency; diagnosed genital anatomical deformities, uncontrolled diabetes mellitus, and history of spinal cord injury, uncontrolled psychiatric disorder, and/or abnormal secondary sexual characteristics; diagnosed prostatic cancer or benign hypertrophy—if suspected by the investigator, refer for medical assessment; acute genitourinary disorder or history of genital surgery; current or history of chronic alcohol and/or drug abuse; suspected or diagnosed chickpea allergy; participation in any other clinical trial during last thirty (30) days; simultaneous participation in another clinical trial; and any condition that in the opinion of the investigator makes the subject unsuitable for inclusion.

Enrolled participants were assigned the investigational product for the full trial at the pre-trial interview. Fenugreek seed extract or placebo was administered orally, as follows. Trigonella foenum-graecum (Fenugreek) seed extract 300mg (dry concentrate 33:1, equivalent to 9.9 g dry herb, standardized to a minimum 50% saponin glycosides, i.e. Fenusides) supplied by Gencor Pacific Ltd. (Hong Kong, PRC), in a two-piece white hard gelatin non-marked capsule size 0. The placebo product contained maltodextrin, also in a size 0 non-marked, hard gelatin capsule. Participants were instructed to take two capsules per day with the evening meal.

During week 0 (baseline), participants' blood was collected (fasting state, after rising) for analysis of pre-treatment blood markers. At the baseline interview the participants completed symptom questionnaires, anthropometic measurements were taken and a strength test conducted.

At the mid-point (week 6), participants completed forms to record any changes to lifestyle and health/medical status, had hormone levels re-tested, and completed the sleep and exercise questionnaires. At completion of the study (week 12), participants completed forms to record any changes to lifestyle and health/medical status, had hormone and other blood parameters re-tested, and completed all other tests as per baseline.

Participants were monitored for compliance with the protocol by a combination of telephone and email communications. Dosing protocol was assessed by comparing returned containers and product to expected returns and intake.

Sample Size

Sample size was calculated based on the AMS total score and was found to require a minimum of forty-eight (48) per treatment group, consequently, to allow for dropouts, a sample size of sixty (60) per sample group was recruited for the study.

Randomization

Once enrolled in the trial, participants were randomly allocated to either the placebo comparator group (n=60) or the active intervention group (n=60). Randomization was performed independently of the investigators using Random Allocation Software, version 1.0, May 2004.

Blinding

Investigators were blinded to the randomization and therefore blinded to which subjects were allocated to the active and treatment arms. Investigational and comparator products were enclosed in TPCs that were identical in function and appearance.

The Primary outcome measures are the AMS sub-scores and total score. Secondary outcome measures are serum testosterone, Sex hormone-binding globulin, and oestrogen pre-intervention and post-intervention. Other secondary outcome measures are quality of life questions, weight/BMI, and safety/tolerability.

The AMS questionnaire consists of seventeen (17) questions in three (3) sub-scales—psychological, somatic, and sexual—the sub-scores with respect to each of these three sub-scales, as well as the total score (the sum of the three sub-scores), were used to assess andropause symptoms. Subjects completed the questionnaires pre-trial (baseline data), upon completion of 6 weeks (mid-trial), and 12 weeks (completion).

Although both the active and placebo groups had a reduction in AMS scores, there was a statistically significant difference (reduction) in the symptom severity in the active treatment group at weeks 6 and 12 in the total AMS score, and all sub-domains, when compared to placebo. See Table 1 as below.

TABLE 1

Aging Male Symptoms (AMS) Questionnaire

| | Active average (Standard Deviation) | | | Placebo average (Standard Deviation) | | |
|---|---|---|---|---|---|---|
| | Baseline | Week 6 | Week 12 | Baseline | Week 6 | Week 12 |
| Psychological sub-score | 10.7 (4.11) | 8.3 (2.78) | 8.0 (3.08)* | 10.5 (4.49) | 10.2 (4.94) | 9.5 (3.84) |
| Somatic sub-score | 18.1 (4.59) | 13.7 (4.10)* | 11.6 (4.42)* | 17.1 (4.87) | 16.4 (5.47) | 14.4 (5.20) |
| Sexual sub-score | 12.8 (4.07) | 9.9 (3.76)* | 8.6 (4.15)* | 12.9 (3.93) | 12.1 (4.01) | 11.3 (4.51) |
| TOTAL score | 41.6 (11.05) | 31.9 (9.59)* | 28.2 (10.12)* | 40.5 (11.18) | 38.7 (12.50) | 35.2 (11.86) |

*Statistically significant < 0.05

Statistical Methods

The primary outcome endpoints (AMS questionnaire responses at baseline, 6, and 12 weeks) were analyzed using an independent samples Mann-Whitney U test for statistical difference at weeks 6 and 12. The DISF-SR was assessed for statistical difference within groups (change from baseline) and between groups, by t-tests.

Change (delta) from baseline to week 6 and baseline to week 12 was calculated for the pathology data and then analyzed between groups using independent sample t-tests for statistical significance. The correlations were analyzed using the Pearson Correlation Co-efficient.

In some embodiments the fenugreek seed extract is administered to a human individual in an amount of from about 300 mg to about 1000 mg per day. In some embodiments, the fenugreek seed extract is administered in an amount of about 600 mg per day. In certain exemplary embodiments, the total daily dose is administered as two approximately equal doses. The fenugreek seed extract can be administered approximately one hour before a meal, for example, about one hour before a morning meal and one hour before an evening meal. In certain exemplary embodiments, the fenugreek extract is administered orally, for example, in the form of a capsule.

EXAMPLE 1.1

Objective: Assess the effectiveness of the fenugreek seed extract on symptoms of Andropause, including libido in aging males, using the AMS QOL questionnaire.

Results: Questionnaires showed a significant reduction in negative or deleterious symptoms in those participants in the active treatment group after 12 weeks. There were significant increases in the sub-scales of the AMS scale in the active treatment group. See also FIG. 1.

The active treatment group showed significant reduction in the psychological sub-scores representative of psychological conditions such as depression, mood swings, nervousness, anxiety, irritability, and poor concentration/memory.

The active treatment group showed significant reduction in the somatic sub-scores representative of somatic conditions such as fatigability, hot flushes, blushing and sweating, adiposity, and reduction in strength and bone/joint complaints.

The active treatment group showed significant reduction in the sexual sub-scores representative of sexual conditions such as reduced libido, erectile dysfunction, and decreased ejaculatory force and volume.

Overall, psychological, somatic, and sexual symptoms did not change in the placebo group at week 12 of treatment (FIG. 1).

In conclusion, the results indicated that the fenugreek seed extract is an effective treatment to enhance the psychological, somatic, and sexual conditions in aging males. The results further indicate that the fenugreek extract is an effective treatment to reduce the symptom severity of psychological, somatic, and sexual conditions in aging males.

EXAMPLE 1.2

Objective: Assess the effectiveness of the fenugreek seed extract on symptoms of Andropause including libido in aging males using DISF-Self Report ("DISF-SR") questionnaire. See Table 2 as below.

The DISF was measured at baseline and week 12. The change from baseline was compared at week 12 for the active vs. placebo. The domains of sexual arousal (p=0.001), sexual drive/relationship (p=0.007), and total score (p=0.006) were significantly higher in the active group after treatment. There were no changes in the domains of sexual cognition, sexual behavior, or orgasm.

TABLE 2

| DISF | Active | | Placebo | |
|---|---|---|---|---|
| N = 111 | Baseline | Week 12 | Baseline | Week 12 |
| Domain 1 (Sexual cognition) | 20.977 (9.72) | 22.14 (9.48) | 17.27 (10.08) | 16.44 (9.93) |
| Domain 2 (Sexual arousal) | 12.89 (7.43) | 16.75 (9.14)* | 10.87 (6.77) | 11.00 (6.84) |
| Domain 3 (Sexual behavior) | 10.95 (6.33) | 12.29 (7.06) | 8.96 (5.11) | 8.52 (5.57) |
| Domain 4 (Orgasm) | 10.55 (5.20) | 12.29 (6.44) | 10.31 (5.12) | 10.44 (5.23) |
| Domain 5 (Sexual drive/Relationship) | 11.07 (3.07) | 12.82 (4.26)* | 10.36 (3.05) | 10.61 (3.56) |
| Total score | 66.23 (24.99) | 76.29 (30.71)* | 57.78 (22.82) | 57.02 (23.68) |

Sexual Drive/Relationship (p = 0.007), Arousal (p = 0.001), Total DISF score (p = 0.006)

The DISF was further analyzed for the individual questions regarding morning erections and frequency of sexual intercourse.

Question 1.2.1 Morning erections—Active and placebo groups at baseline reported 1 per week; by week 12, active group reported significant change to 2-3 per week, with no change in the placebo group (p=0.001). See FIG. 2.

Question 1.2.2 Frequency of sexual intercourse—Active and placebo groups reported approximately 1-2 per month; by week 12, active group reported significant increase to almost 1 per week. (p=0.004). See FIG. 3.

Figure 2:
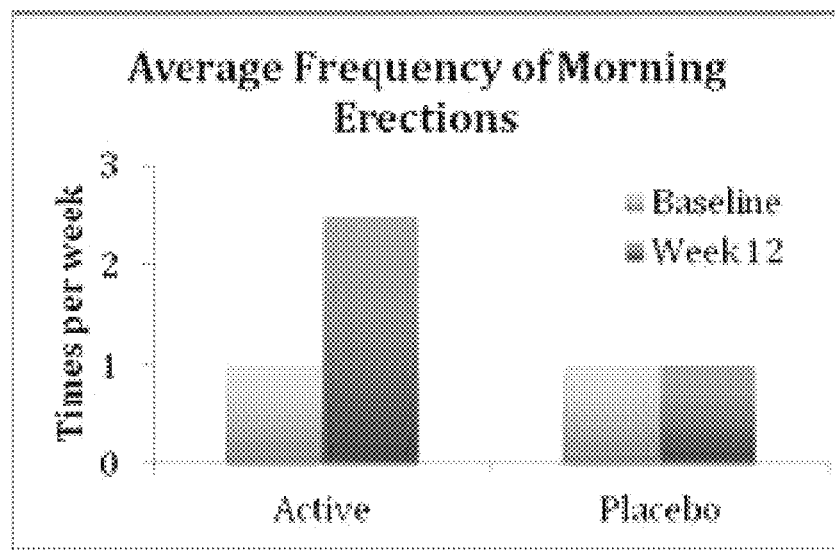
FIG. 2 depicts average weekly frequency of morning erections for male subjects treated as stated for FIG. 1. Baseline vs. week 12 are presented top to bottom in the legend, corresponding to left to right in the bar graph.
Figure 3:
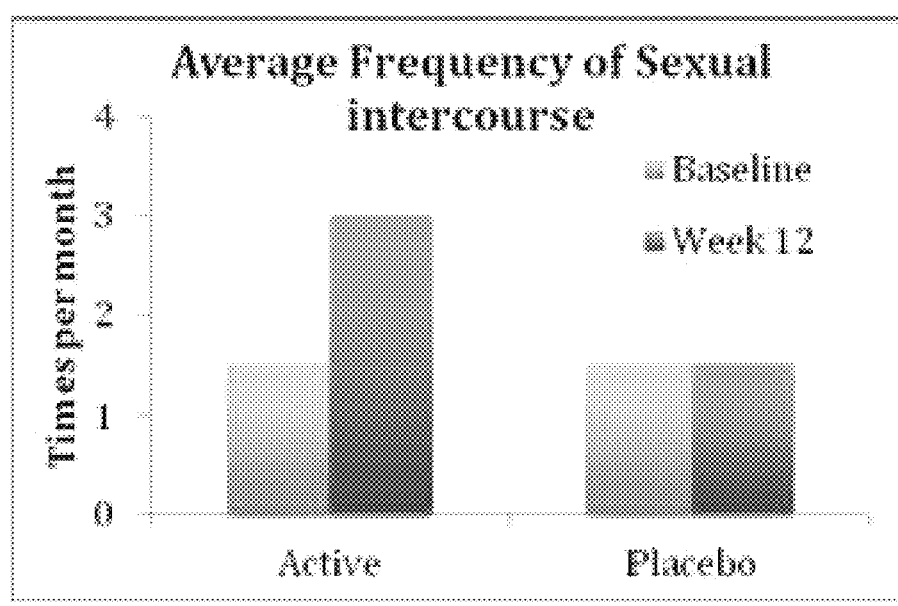
FIG. 3 depicts average monthly frequency of sexual intercourse for male subjects treated as stated for FIG. 1. Baseline vs. week 12 are presented top to bottom in the legend, corresponding to left to right in the bar graph.

The results as shown in FIGS. 2 and 3 correlated well with the similar questions (16 and 17) in the AMS questionnaire.

Overall, the questionnaires showed a significant increase in those participants in the active treatment group after 12 weeks. There were significant increases in the sub-analysis of the five (5) domains of the DISF-SR; sexual cognition, sexual arousal, sexual experience, orgasm, and sexual drive/relationship at week 12. Overall, sexual functioning did not change in the placebo group; the placebo group showed no difference in the DISF-SR domain scores at week 12 of treatment.

In conclusion, the results indicated that the fenugreek extract is an effective treatment to improve sexual functions such as sexual cognition, sexual arousal, sexual behavior, orgasm, sexual drive/relationship in aging males.

EXAMPLE 1.3

Objective: Assess the effectiveness of the fenugreek extract on symptoms of Andropause including libido in aging males on serum hormone levels of testosterone. See Table 3 as below.

Serum hormone levels of Testosterone were tested at baseline, 6, and 12 weeks. R. Sodergard et al., *Calculation of free and bound fractions of testosterone and estradiol-17 beta to human plasma proteins at body temperature*, 16 J. STEROID BIOCHEM. 801-10 (1982). Additional pathology was tested at baseline and week 12 including glucose, cholesterol, lipid studies, electrolytes, and liver function, as well as full blood counts. Strength in both the left and right hand was measured using a dynamometer at all three time points. Qualitative contextual information, including body weight, waist-to-hip ratio, diet, other lifestyle changes, concomitant medical conditions, and medication changes, were also recorded at each time-point.

TABLE 3

| | Pathology Data | | | | | |
|---|---|---|---|---|---|---|
| | N = 97 | | | | | |
| | Active | | | Placebo | | |
| Mean (SD) | Baseline | Week 6 | Week 12 | Baseline | Week 6 | Week 12 |
| Testosterone [nmol/L] | 12.34 (4.42) | 12.93 (4.88) | 13.81* (5.05) | 13.22 (5.13) | 13.48 (5.53) | 12.38 (5.24) |
| Average Δ | — | 0.83 (3.24) | 1.61 (3.31) | — | 0.40 (3.17) | −0.76 (2.96) |
| Free Testosterone [nmol/L] | 0.24 (0.07 | 0.25 (0.08) | 0.26* (0.08) | 0.25 (0.09) | 0.32 (0.48) | 0.23 (0.07) |
| Average Δ | — | 0.005 (0.067) | 0.023 (0.064) | — | 0.069 (0.010) | −0.020 (0.068) |

As shown in Table 3, there was a significant increase from baseline in the active group for Testosterone (p<0.001) and Free Testosterone (p=0.002) at week 12 compared to placebo.

Analysis of the sex hormone levels after 12 weeks of treatment showed a significant increase in Testosterone and Free Testosterone levels in the active group compared to the placebo group. There were no significant differences in any hormones in the placebo group.

Other pathology: no changes were seen at the week 6 or 12 time-points in either treatment group in the other pathology parameters including glucose, cholesterol, triglycerides, or LDL or HDL concentrations.

In conclusion, the results indicated that the fenugreek or fenugreek seed extract is an effective treatment to enhance Testosterone and Free Testosterone levels and to prevent further declines of sexual hormones such Testosterone and Free Testosterone.

Fenugreek or fenugreek seed extract may be formulated as a pharmaceutical or nutraceutical composition, including a pharmaceutically or nutraceutically acceptable carrier, respectively. In one embodiment of a pharmaceutical composition containing fenugreek or fenugreek seed extract, a suitable level of fenugreek seed extract may range from about 0.1% by weight to about 10% by weight, based on the total weight of the composition.

"Pharmaceutically or nutraceutically acceptable carrier" means any carrier, diluents, or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The nutraceutical compositions disclosed herein may be administered in combination with a nutraceutically acceptable carrier. The active ingredients in such formulation s may comprise from 1% by weight to 99% by weight, or alternatively, 0.1% by weight to 99.9% by weight.

Suitable methods of administration include, but are not limited to, sublingual, buccal, oral, and the like.

Suitable dosage forms include tablets, capsules, solutions, suspensions, powders, gums, and confectionaries. Other sublingual delivery systems include, but are not limited to, dissolvable tabs under and on the tongue, liquid drops, and beverages. Edible films, hydrophilic polymers, oral dissolvable films, or oral dissolvable strips can be used.

Liquid-based nutritional dosage forms for oral administration can be prepared in water, juices, or other aqueous vehicles. Useful liquid forms include solutions, suspensions, emulsions, and the like. Microemulsions and microencapsulations are contemplated. In addition, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional or dietary supplement compositions can be in the form of a solution, emulsion, syrup, gel, or elixir including or containing, together with the above enumerated ingredients or compounds, wetting agents, surfactants, dispersants, emulsifiers, sweeteners, and coloring and flavoring agents. Various liquid and powder nutritional compositions can be prepared by conventional methods.

The dosage forms may or may not be presented in unit dosage forms and/or servings, depending on the delivery system and/or the end user. Unit dosage, for example, would be applicable to a ready-to-drink ("RTD") delivery system. In such form, the preparation is subdivided into unit doses containing appropriate quantities of the nutritional or active component(s). The unit dosage form can be a packaged preparation, the package containing discrete quantities of preparation.

Solid dosage forms may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. For example, the active agent may be combined with at least one excipient such as fillers, binders, humectants, disintegrating agents, solution retarders, absorption accelerators, wetting agents, surfactants, dispersants, emulsifiers, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like. The usefulness of such excipients is well known in the art.

In one embodiment, the dosage form may be in the form of a liquid. In accordance with this embodiment, a method of making a liquid dosage form is provided.

Liquid dosage forms can be prepared in water or other aqueous vehicles. In addition to the above enumerated ingredients or compounds, liquid nutritional composition can include suspending agents such as, for example, methylcellulose, alginates, tragacanth, pectin, kelgin, carrageenan, acacia, polyvinylpyrolidone, polyvinyl alcohol, and the like. The liquid dosage forms can be in the form of a solution, emulsion, syrup, gel, or elixir, including or containing, together with the above enumerated ingredients or compounds, wetting agents, sweeteners, and coloring and flavoring agents. Various liquid and powder dosage forms can be prepared by conventional methods. Various RTD formulations are contemplated.

The embodiments described herein can be assembled from liquids obtained through several separate processes, including, but not limited to, extracts.

The dosage forms suitable for parenteral administration may be prepared by manufacturing techniques which are well known to those skilled in the art.

Reference is made to the latest edition of Remington's Pharmaceutical Sciences (Mack Publishing Co., Easton, PA); however, nothing within Remington's Pharmaceutical Sciences should be understood to limit the meaning of any term of any of the appended claims beyond its broadest reasonable construction as understood by those skilled in the art.

While in the foregoing specification this invention has been described in relation to certain embodiments thereof, and many details have been put forth for the purpose of illustration, it will be apparent to those skilled in the art that the invention is susceptible to additional embodiments, and that certain of the details described herein can be varied considerably without departing from the basic principles of the invention.

All references cited herein are incorporated by reference in their entirety, but nothing within any such references should be understood to limit the meaning of any of the appended claims beyond its broadest reasonable construction as understood by those skilled in the art. The present invention may be embodied in other specific forms without departing from the spirit or essential attributes thereof, and, accordingly, reference should be made to the appended claims, rather than to the foregoing specification, as indicating the scope of the invention.

We claim:

1. A method of preventing further decline of sexual hormones in a male human subject, and/or improving sexual hormonal level in a male human subject, said male aged about 40 years or older, said method comprising administering fenugreek or fenugreek seeds, or an extract of fenugreek or fenugreek seeds, to the male human subject in need thereof, wherein the daily dose of the extract is from about 300 mg to about 600 mg.

2. The method as claimed in claim 1, wherein the sexual hormones comprise one or more of Testosterone and Free Testosterone, wherein serum Testosterone (nmol/L) is increased at least 10% over 12 weeks.

3. The method as claimed in claim 1, wherein the fenugreek or fenugreek seeds, or the extract of the fenugreek or fenugreek seeds, is formulated into a dosage form selected from the group comprising solid oral formulation, liquid oral formulation, parenteral formulation, phytoceutical formulation, nutraceutical formulation, and foodstuff, or any useful combinations thereof.

\* \* \* \* \*